United States Patent
Grosch et al.

(10) Patent No.: US 6,710,002 B2
(45) Date of Patent: *Mar. 23, 2004

(54) METHOD FOR REGENERATING A ZEOLITIC CATALYST

(75) Inventors: Georg Heinrich Grosch, Bad Duerkheim (DE); Ulrich Mueller, Neustadt (DE); Andreas Walch, Heidelberg (DE); Norbert Rieber, Mannheim (DE); Wolfgang Harder, Weinheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 45 days.

This patent is subject to a terminal disclaimer.

(21) Appl. No.: 10/061,282

(22) Filed: Feb. 4, 2002

(65) Prior Publication Data

US 2002/0082159 A1 Jun. 27, 2002

Related U.S. Application Data

(63) Continuation of application No. 09/424,854, filed as application No. PCT/EP98/03396 on Jun. 5, 1998, now Pat. No. 6,380,119.

(30) Foreign Application Priority Data

Jun. 6, 1997 (DE) .......................... 197 23 949

(51) Int. Cl.⁷ ................................. B01L 29/90
(52) U.S. Cl. .................. 502/49; 502/38; 502/52; 502/56; 502/22; 502/29
(58) Field of Search .............. 502/38, 49, 52, 502/56, 22, 29

(56) References Cited

U.S. PATENT DOCUMENTS

| 4,300,014 A | 11/1981 | Yamasaki et al. |
| 4,447,669 A | 5/1984 | Hamon et al. |
| 4,610,972 A | 9/1986 | Hughes |
| 4,833,260 A | 5/1989 | Neri et al. |
| 5,073,529 A | 12/1991 | Miller et al. |
| 5,075,268 A | 12/1991 | Kurashige et al. |
| 5,087,783 A | 2/1992 | Johnson et al. |
| 5,741,749 A | 4/1998 | Crocco et al. |
| 5,859,265 A | 1/1999 | Muller et al. |
| 6,066,586 A | 5/2000 | Hashimoto et al. |
| 6,114,265 A | 9/2000 | Steffens et al. |
| 6,380,119 B1 * | 4/2002 | Grosch et al. ............... 502/49 |

FOREIGN PATENT DOCUMENTS

| DE | 44 25 672 A | 1/1996 |
| EP | 0 604 689 A | 7/1994 |
| EP | 0 743 094 A | 11/1996 |
| EP | 0 790 075 A | 8/1997 |

OTHER PUBLICATIONS

Patent Abstract of Japan, vol. 015, No. 306 (c–0856), Aug. 6, 1991 & JP 03 114536 A (Mitsui Toatsu Chem Inc), May, 15, 1991.

* cited by examiner

Primary Examiner—Tom Dunn
Assistant Examiner—Christina Ildebrando
(74) Attorney, Agent, or Firm—Oblon, Spivak, McClelland, Maier & Neustadt, P.C.

(57) ABSTRACT

A process for regenerating a zeolite catalyst comprises the following stages:

(I) Heating a partially or completely deactivated catalyst to 250–600° C. in an atmosphere which contains less than 2% by volume of oxygen, (II) treating the catalyst at from 250 to 800° C., preferably from 350 to 600° C., with a gas stream which contains from 0.1 to 4% by volume of an oxygen-donating substance or of oxygen or of a mixture of two or more thereof, and (III) treating the catalyst at from 250 to 800° C., preferably from 350 to 600° C., with a gas stream which contains from more than 4 to 100% by volume of an oxygen-donating substance or of oxygen or of a mixture of two or more thereof.

12 Claims, No Drawings

METHOD FOR REGENERATING A ZEOLITIC CATALYST

The present invention relates to a process for regenerating a zeolite catalyst, in particular a zeolite catalyst which was used in the epoxidation of olefins with a hydroperoxide, in particular of propylene with hydrogen peroxide. The regeneration is carried out by controlled combustion of the predominantly organic coatings responsible for the deactivation in an inert gas atmosphere which contains exactly defined amounts of oxygen or oxygen-donating substances.

When carrying out reactions in the presence of catalysts, in particular in the presence of catalysts which have micropores, such as titanium silicalite having, for example, the MFI structure or titanium-containing zeolites having, for example, the BEA structure, the catalysts may be deactivated by, in particular, organic coatings. The major part of these organic coatings can be removed by calcination of the catalyst or by washing with solvents (M. G. Clerici, G. Bellussi and U. Romano, J. Catal. 129 (1991), 159–167).

Furthermore, EP-A 0 743 094 describes the regeneration of a titanium-containing molecular sieve which was used in the catalysis of an oxidation reaction, for example the epoxidation of an olefin with hydrogen peroxide or with another active oxygen compound. According to this publication, the regeneration of the deactivated catalysts which is described there is carried out by combustion by means of calcination of the organic coatings present thereon using molecular oxygen, a calcination temperature of more than 150° C. and less than 400° C. being used.

Moreover, JP-A 0 31 14 536 describes the regeneration of a titanium silicalite epoxidation catalyst by combustion of the coatings at from 400 to 500° C. or by washing of the catalysts at temperatures above the epoxidation temperature. The solvents stated there are water, alcohols, ketones, aliphatic and aromatic hydrocarbons, halogen-containing hydrocarbons, esters, nitriles or acids.

Furthermore, DE-A 44 25 672 mentions the regeneration of a catalyst used for epoxidation, in particular of propylene, by combustion thereof in an oxygen-containing atmosphere at elevated temperatures.

However, the prior art regeneration processes have some aspects which are undesired in practice, in particular where catalysts containing micropores, for example the titanium silicalites used in particular in epoxidation, are to be regenerated.

Some of the catalysts preferably used for epoxidations, for example a titanium silicalite having the MFI structure or a titanium silicalite having the BEA structure, have micropores with diameters of from about 0.5 to about 0.6 nm of from about 0.6 to about 0.7 nm. In both cases, however, it is impossible completely to remove oligomeric or even polymeric byproducts of the reactions catalyzed by these catalysts, in particular of the epoxidation, merely by washing with solvents at elevated temperatures.

The above statements are applicable in particular to catalysts having micropores but, depending on the molecular weight and on the dimensions of the oligomeric or polymeric byproducts forming during the reaction, are also applicable to catalysts having mesopores and/or macropores.

However, if it is intended to remove these organic coatings completely, this is possible only by combustion thereof with oxygen or with oxygen-donating substances. The regeneration of a highly selective zeolite catalyst having a specific structure by combustion at elevated temperatures is however difficult, since complete or local overheating of the catalyst may lead to loss of selectivity as a result of the partial or, in extreme cases, complete destruction of the structure inherent in the zeolite catalysts, which destruction occurs with such overheating. If, in order to avoid such overheating, the combustion is carried out at below 400° C., the coatings are not completely removed during relatively short calcination times. Complete removal of the coatings by very long calcination at below 400° C. is however of no commercial interest.

It is an object of the present invention to provide a process for regenerating a zeolite catalyst at elevated temperatures, which ensures complete removal of the organic coatings even during relatively short calcination times. The calcination should take place in a controlled manner so that local overheating and hence irreversible damage to the catalyst, which leads to loss of selectivity, to increased formation of byproducts and hence to substantially more rapid deactivation of the regenerated catalyst when used again, is avoided.

We have found that this object is achieved by the novel process.

The present invention therefore relates to a process for regenerating a zeolite catalyst which comprises the following stages (I) and (II):

(I) Heating a partially or completely deactivated catalyst to 250–600° C. in an atmosphere which contains less than 2% by volume of oxygen and (II) treating the catalyst at from 250 to 800° C., preferably from 350 to 600° C., with a gas stream which contains from 0.1 to 4% by volume of an oxygen-donating substance or of oxygen or of a mixture of two or more thereof.

Preferably, the novel process comprises a further stage (III):

(III) Treating the catalyst at from 250 to 800° C., preferably from 350 to 600° C., with a gas stream which contains from more than 4 to 100% by volume of an oxygen-donating substance or of oxygen or of a mixture of two or more thereof.

There are no particular restrictions with regard to the zeolite catalysts regenerated in the present process.

Zeolites are known to be crystalline aluminosilicates having ordered channel and cage structures which possess micropores which are preferably smaller than about 0.9 nm. The network of such zeolites is composed of $SiO_4$ and $AlO_4$ tetrahedra which are linked by common oxygen bridges. An overview of the known structures is given, for example, in W. M. Meier, D. H. Olson and Ch. Baerlocher, Atlas of Zeolite Structure Types, Elsevier, 4th Edition, London 1996.

Zeolites which contain no aluminum and in which some of the Si(IV) in the silicate framework has been replaced by titanium as Ti(IV) are also known. These titanium zeolites, in particular those having a crystal structure of the MFI type, and possibilities for their preparation are described, for example in EP-A 0 311 983 or EP-A 405 978. In addition to silicon and titanium, such materials may also contain additional elements, for example aluminum, zirconium, tin, iron, cobalt, nickel, gallium, boron or small amounts of fluorine. In the zeolite catalysts preferably regenerated by the novel process, some or all of the titanium of the zeolite may be replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is as a rule from 0.01:1 to 0.1:1.

It is known that titanium zeolites having the MFI structure can be identified by particular X-ray diffraction patterns and additionally by an infrared (IR) skeletal vibration band at about 960 cm$^{-1}$ and thus differ from alkali metal titanates or crystalline and amorphous TiO$_2$ phases.

Preferably Ti, V, Cr, Nb and Zr zeolites, particularly preferably Ti zeolites, and especially Ti zeolites as used in particular for the epoxidation of olefins, are regenerated by the novel process.

Specific examples are Ti, V, Cr, Nb or Zr zeolites having the pentasil zeolite structure, in particular the types allocated by X-ray analysis to the BEA, MOR, TON, MTW, FER, MFI, MEL, CHA, ERI, RHO, GIS, BOG, NON, EMT, HEU, KFI, FAU, DDR, MTT, RUT, LTL, MAZ, GME, NES, OFF, SGT, EUO, MFS, MCM-22 or MFI/MEL mixed structure and ITQ-4, those having the MFI structure, BEA structure, MEL structure, ITQ-4 or MFI/MEL mixed structure being regarded as particularly preferred. Zeolites of this type are described, for example, in the above-mentioned publication by W. M. Meier et al.

Particularly preferred catalysts are specifically the Ti-containing catalysts, which are referred to in general as TS-1, TS-2, TS-3, TS-48 and TS-12, and Ti zeolites having a skeletal structure isomorphous with beta-zeolite.

Further zeolite catalysts which may be regenerated in the process of the present invention are described, inter alia, in U.S. Pat. No. 5,430,000 and WO 94/29408, the content of which in this context is hereby incorporated herein by reference.

Further titanium-containing zeolites to be mentioned are those having the structure of ZSM-48, ZSM-12, ferrierite or β-zeolite and of mordenite.

It is of course also possible to regenerate mixtures of two or more catalysts, in particular of the above-mentioned catalysts, in the novel process.

There are also no particular restrictions with regard to the pore sizes or the pore size distribution of the zeolite catalysts regenerated according to the invention. Thus, catalysts which have micropores, mesopores or even macropores, for example Ti-containing SiO$_2$ oxides having macropores, can be regenerated in the novel process. The novel process can be particularly advantageously used for regenerating catalysts containing micropores. These include catalysts which contain exclusively micropores and those which have micropores and mesopores or micropores and macropores or micropores, mesopores and macropores. The term micropores as used in the present application describes pores having a diameter of 2 nm or less. The term macropores relates to pores having a diameter greater than about 50 nm, and the term mesopores relates to pores having a diameter of from >2 nm to about 50 nm, corresponding in each case to the definition according to Pure Appl. Chem. 45 (1976), 71 et seq., in particular 79.

It is also possible to regenerate the following zeolite catalysts by means of the novel process:

Oxidation catalysts having a zeolite structure, as described in DE-A 196 23 611.8, which are hereby fully incorporated herein by reference with regard to the catalysts described therein.

These are oxidation catalysts based on titanium silicates or vanadium silicates having a zeolite structure, reference being made to the structures stated above as being preferred with regard to the zeolite structure. These catalysts have been shaped by compacting shaping processes.

Compacting shaping processes which may be used are in principle all methods for appropriate shaping, as generally used for catalysts. Preferred processes are those in which the shaping is effected by extrusion in conventional extruders, for example to give extrudates having a diameter of, usually, from 1 to 10 mm, in particular from 2 to 5 mm. If binders and/or assistants are required, the extrusion is advantageously preceded by a mixing or a kneading process. If required, a calcination step is also carried out after the extrusion The extrudates obtained are, if desired, comminuted, preferably to granules or chips having a particle diameter of from 0.5 to 5 mm, in particular from 0.5 to 2 mm. These granules or these chips and also catalyst moldings produced by other methods contain virtually no particle fractions finer than those having a minimum particle diameter of 0.5 mm.

In a preferred embodiment, the molded oxidation catalyst used contains up to 10% by weight, based on the total weight of the catalyst, of binders. Particularly preferred binder contents are from 0.1 to 7, in particular from 1 to 15, % by weight Suitable binders are in principle all compounds used for such purposes, preference being given to compounds, in particular oxides, of silicon, of aluminum, of boron, of phosphorus, of zirconium and/or of titanium. Of particular interest as a binder is silica, where the SiO$_2$ can be introduced into the shaping step as silica sol or in the form of tetraalkoxysilanes. Oxides of magnesium and of beryllium, and clays, e.g. montmorillonites, kaolins, bentonites, halloysites, dickites, nacrites and anauxites, may also be used as binders.

Examples of assistants for the compacting shaping processes are extrusion aids, a conventional extrusion aid being methylcellulose. Such aids generally undergo complete combustion in a subsequent calcination step.

Typically, the stated titanium and/or vanadium zeolites are prepared by reacting an aqueous mixture of an SiO$_2$ source, a titanium or vanadium source, such as titanium dioxide or a corresponding vanadium oxide, and a nitrogen-containing organic base (template compound), e.g. tetrapropylammonium hydroxide, if necessary with the addition of basic compounds, in a pressure-resistant container at elevated temperatures over a period of from several hours to a few days, the crystalline product being formed. This is filtered off, washed, dried and combusted at elevated temperatures to remove the organic nitrogen base. In the powder thus obtained, some or all of the titanium or the vanadium is present within the zeolite skeleton in varying amounts having four-, five- or six-fold coordination. Repeated washing with hydrogen peroxide solution containing sulfuric acid can be carried out subsequently to improve the catalytic behavior, after which the titanium or vanadium zeolite powder must again be dried and subjected to combustion; this may be followed by a treatment with alkali metal compounds in order to convert the zeolite from the H form into the cationic form. The titanium or vanadium zeolite powder thus prepared is then molded as described above for the purposes of the present invention.

Furthermore, oxidation catalysts based on titanium or vanadium silicates having a zeolite structure and containing from 0.01 to 30% by weight of one or more noble metals selected from the group consisting of ruthenium, rhodium, palladium, osmium, iridium, platinum, rhenium, gold and silver, which likewise have been shaped by compacting shaping processes, can also be regenerated. Such catalysts are described in DE-A 196 23 609.6, which is hereby fully incorporated herein by reference with regard to the catalysts described therein.

The statements made above in connection with DE-A 196 23 611.8 are applicable with regard to the compacting shaping processes, the binders and the assistants, and the structure of the oxidation catalysts.

The oxidation catalyst described there contains from 0.01 to 30, in particular from 0.05 to 15, especially from 0.01 to 8, % by weight, based in each case on the amount of the titanium or vanadium zeolites, of the stated noble metals. Palladium is particularly preferred here. The noble metals may be applied to the catalyst in the form of suitable noble metal components, for example in the form of water-soluble salts, during or after the compacting shaping step.

In many cases, however, it is most advantageous for the noble metal components to be applied only after the shaping step to the catalyst moldings, particularly when a high temperature treatment of the noble metal-containing catalyst is undesirable. The noble metal components can be applied to the molded catalyst in particular by ion exchange, impregnation or spraying on. The application can be effected by means of organic solvents, aqueous ammoniacal solutions or supercritical phases, for example carbon dioxide.

By using these above-mentioned methods, it is entirely possible to produce different types of noble metal-containing catalysts. Thus, a type of coated catalyst can be produced by spraying the noble metal solution onto the catalyst moldings. The thickness of this noble metal-containing coat can be substantially increased by impregnation, whereas the catalyst particles are coated substantially uniformly with noble metal over the molding cross-section in the case of ion exchange.

The following catalysts can also be regenerated according to the invention: A molding which contains at least one porous oxidic material and is obtainable by a process which comprises the following stages:

(I) Addition of a mixture containing at least one alcohol and water to a mixture containing a porous oxidic material or a mixture of two or more thereof, and (II) kneading, molding, drying and calcining of the mixture after addition according to stage (I).

The preparation of the moldings described above starting from a porous oxidic material in powder form comprises the formation of a plastic material which contains at least one porous oxidic material, a binder, a mixture containing at least one alcohol and water, if required one or more organic viscosity-increasing substances and further additives known from the prior art.

The plastic material obtained by thorough mixing, in particular kneading, of the above components is preferably molded by extrusion pressing or extrusion and the molding obtained is then dried and finally calcined.

There are no particular restrictions with regard to the porous oxidic materials which may be used for producing the molding, provided that it is possible to produce a molding as described herein starting from these materials.

The porous oxidic material is preferably a zeolite, particularly preferably a titanium-, zirconium-, chromium-, niobium-, iron- or vanadium-containing zeolite, in particular a titanium silicalite.

With regard to the zeolites, in particular their structure and composition, reference is once again made to the above discussion of the zeolites discussed in connection with the application and to be regenerated by the novel process.

Usually, the stated titanium, zirconium, chromium, niobium, iron and vanadium zeolites are prepared by reacting an aqueous mixture of an $SiO_2$ source, a titanium, zirconium, chromium, niobium, iron or vanadium source, e.g. titanium dioxide or a corresponding vanadium oxide, zirconium alcoholate, chromium oxide, niobium oxide or iron oxide, and a nitrogen-containing organic base as a template (template compound), e.g. tetrapropylammonium hydroxide, if required with the addition of basic compounds, in a pressure-resistant container at elevated temperatures over a period of from several hours to a few days, a crystalline product being formed. This is filtered off, washed, dried and subjected to combustion at elevated temperatures to remove the organic nitrogen base. In the powder thus obtained, some or all of the titanium or of the zirconium, chromium, niobium, iron and/or vanadium is present within the zeolite skeleton in varying amounts having 4-, 5- or 6-fold coordination. Repeated washing with hydrogen peroxide solution containing sulfuric acid can be carried out subsequently to improve the catalytic behavior, after which the titanium or zirconium, chromium, niobium, iron or vanadium zeolite powder must again be dried and subjected to combustion; this may be followed by a treatment with alkali metal compounds in order to convert the zeolite from the H form into the cation form. The titanium or zirconium, chromium, niobium, iron or vanadium zeolite powder thus prepared is then processed to a molding as described above.

Preferred zeolites are titanium, zirconium, chromium, niobium or vanadium zeolites, particularly preferably those having the pentasil zeolite structure, in particular the types allocated by X-ray analysis to the BEA, MOR, TON, MTW, FER, MFI, MEL, CHA, ERI, RHO, GIS, BOG, NON, EMT, HEU, KFI, FAU, DDR, MTT, RUT, LTL, MAZ, GME, NES, OFF, SGT, EUO, MFS, MCM-22 or MFI/MEL mixed structure. Zeolites of his type are described, for example, in the above-mentioned publication by Meier and Olson. Titanium-containing zeolites having the structure ZSM-48, ZSM-12, ferrierite or β-zeolite and of mordenite are also possible. Such zeolites are described, inter alia, in U.S. Pat. No. 5,430,000 and WO 94/29408, the content of which in this context is hereby fully incorporated herein by reference.

Furthermore, there are no particular restrictions with regard to the pore structure of the moldings to be regenerated according to the invention, i.e. the novel moldings may have micropores, mesopores, macropores, micro- and mesopores, micro- and macropores or micro-, meso- and macropores, the definition of the terms mesopores and macropores also corresponding to that in the above-mentioned literature according to Pure Appl. Chem. and denoting pores having a diameter of from >2 nm to about 50 nm, and > about 50 nm, respectively.

Furthermore, a material based on a silicon-containing oxide having mesopores and a silicon-containing xerogel may be regenerated by means of the novel process.

Silicon-containing oxides which have mesopores and also contain Ti, V, Zr, Sn, Cr, Nb or Fe, in particular Ti, V, Zr, Cr, Nb or a mixture of two or more thereof, are particularly preferred.

Suitable binders are in principle all compounds used to date for such purposes. Particularly preferably used compounds are oxides of silicon, of aluminum, of boron, of phosphorus, of zirconium and/or of titanium. Silica is of particular interest as a binder, and the $SiO_2$ can be introduced into the shaping step as silica sol or in the form of tetraalkoxysilanes. Furthermore, oxides of magnesium and of beryllium, and clays, e.g. montmorillonites, kaolins, bentonites, halloysites, dickites, nacrites and anauxites, may be used as binders.

However, a metal acid ester or a mixture of two or more thereof is preferably added as the binder in stage (I) of the novel process. Particular examples thereof are orthosilicic acid esters, tetraalkoxysilanes, tetraalkyl titanates, trialkyl aluminates, tetraalkyl zirconates or a mixture of two or more thereof.

However, tetraalkoxysilanes are particularly preferably used as the binder in the present invention. Specific examples are tetramethoxysilane, tetraethoxysilane, tetrapropoxysilane and tetrabutoxysilane, the analogous tetraalkoxytitanium and tetraalkoxyzirconium compounds and timethoxy-, triethoxy-, tripropoxy- and tributoxyaluminum, with tetramethoxysilane and tetraethoxysilane being particularly preferred.

The molding preferably contains up to about 80, particularly preferably from about 1 to about 50, in particular from about 3 to about 30, % by weight, based on the total weight of the molding, of binder, the amount of binder being determined by the resulting metal oxide.

The preferably used metal acid ester is employed in an amount such that the resulting metal oxide content in the molding is from about 1 to about 80, preferably from about 2 to about 50, in particular from about 3 to about 30, % by weight, based on the total weight of the molding.

As is evident from the above, it is of course also possible to use mixtures of two or more of the above-mentioned binders.

It is essential for the production of these moldings that a mixture containing at least on alcohol and water is used as the pasting agent. The alcohol content of this mixture is in general from about 1 to about 80, preferably from about 5 to about 70, in particular from about 10 to about 60, % by weight, based on the total weight of the mixture.

Preferably, the alcohol used corresponds to the alcohol component of the metal acid ester preferably used as a binder, but another alcohol may also be used.

There are no restrictions at all with regard to the alcohols which may be used, provided that they are water-miscible. Accordingly, both monoalcohols of 1 to 4 carbon atoms and water-miscible polyhydric alcohols may be used. In particular, methanol, ethanol, propanol, n-butanol, isobutanol, tert-butanol and mixtures of two or more thereof are used.

The organic viscosity-increasing substance used may likewise be any prior art substance suitable for this purpose. Such substances are preferably organic, in particular hydrophilic polymers, e.g. cellulose, starch, polyacrylates, polymethacrylates, polyvinyl alcohol, polyvinylpyrrolidone, polyisobutene and polytetrahydrofuran. These substances primarily promote the formation of a plastic mass during the kneading, molding and drying steps by bridging the primary particles and moreover ensure the mechanical stability of the molding during molding and drying. These substances are removed from the molding during calcination.

Amines or amine-like compounds, e.g. tetraalkylammonium compounds or amino alcohols, and carbonate-containing substances, such as calcium carbonate, may be introduced as further additives. Such further additives are described in EP-A 0 389 041, EP-A 0 200 260 and WO 95/19222, which are hereby fully incorporated by reference in the context of the present application.

Instead of basic additives, it is also possible to use acidic additives. These can, inter alia, effect a more rapid reaction of the metal acid ester with the porous oxidic material. Preferred organic acidic compounds are those which can be burnt out after the molding step by calcination. Carboxylic acids are particularly preferred. Of course, mixtures of two or more of the above-mentioned additives may also be incorporated.

The order of addition of the components of the material containing the porous oxidic material is not critical. It is possible either first to add the binder, then the organic viscosity-increasing substance, if required the additive and finally the mixture containing at least one alcohol and water or to interchange the order with regard to the binder, the organic viscosity-increasing substance and the additives.

After the addition of the binder to the porous oxide powder, to which the organic viscosity-increasing substance may already have been added, the material, which is generally still in powder form, is homogenized for from 10 to 180 minutes in a kneader or extruder. As a rule, the procedure is carried out from about 10° C. to the boiling point of the pasting agent and at atmospheric pressure or slightly superatmospheric pressure. The remaining components are then added, and the mixture thus obtained is kneaded until an extrudable, plastic material has formed.

In principle, the kneading and the molding can be effected using all conventional kneading and molding apparatuses or methods, of which there are many known in prior art and used for the production of, for example, catalyst moldings generally.

However, processes in which the molding is effected by extrusion in conventional extruders, for example to give extrudates having a diameter of usually from about 1 to about 10 mm, in particular from about 2 to about 5 mm, are preferred. Such extrusion apparatuses are described, for example, in Ullmanns Enzyklopädie der Technischen Chemie, 4th Edition, Vol. 2, page 295 et seq., 1972. In addition to the use of an extruder, an extrusion press is preferably also used for the molding.

After the end of extrusion pressing or extrusion, the moldings obtained are dried at in general from about 30 to 140° C. (from 1 to 20 h, atmospheric pressure) and calcined at from about 400 to about 800° C. (from 3 to 10 h, atmospheric pressure).

The strands or extrudates obtained can of course be comminuted. They are preferably comminuted to give granules or chips having a particle diameter of from 0.1 to 5 mm, in particular from 0.5 to 2 mm.

These granules or these chips and also moldings produced by other methods contain virtually no particle fractions finer than those having a minimum particle diameter of about 0.1 mm.

In the novel process, it is possible to use both catalysts in powder form, which were used as suspension, and catalysts packed in a fixed bed, in the form of a molding, and catalysts crystallized on nets, for example a stainless steel, Kanthal or packings, and coated catalysts consisting of an inert core of $SiO_2$, $\alpha$-$Al_2O_3$, highly calcined $TiO_2$ or steatite and an active catalyst coat which comprises a zeolite, preferably a zeolite as defined above, which are regenerated.

If the catalyst was used in a suspension procedure, it must first be separated off from the reaction solution by a separation step, for example filtration or centrifuging. The at least partially deactivated catalyst powder thus obtained can then be regenerated. The stages carried out at elevated temperatures during the regeneration process are preferably effected in rotary furnaces in the case of such catalyst powders. In the regeneration of a catalyst used in a suspension procedure, it is particularly preferable, in order to couple the reaction in the suspension procedure and the novel regeneration process, continuously to remove from the reaction a part of the at least partially deactivated catalyst, to regenerate it externally by means of the novel process and to recycle the regenerated catalyst to the reaction in the suspension procedure.

In addition to the regeneration of catalysts in powder form, the novel process can also be used for regenerating catalysts as moldings, for example those which are packed in a fixed bed. In the regeneration of a catalyst packed in a fixed bed, regeneration is preferably effected in the reaction apparatus itself, it being unnecessary either to remove or to install the catalyst for this purpose, so that it is subjected to no additional mechanical stress at all. In the regeneration of the catalyst in the reaction apparatus itself, the reaction is first stopped, any reaction mixture present is removed, the regeneration is carried out and the reaction is then continued.

Both in the regeneration of catalyst powders and in the regeneration of catalysts in molded form the novel regeneration takes place essentially in an identical manner.

In stage (I), the catalyst is heated to a temperature of from about 250 to about 600° C., preferably from about 400 to 550° C., in particular from about 450 to 500° C., either in the reaction apparatus or in an external furnace, in an atmosphere which contains less than 2, preferably less than 0.5, in particular less than 0.2, % by volume of oxygen. The heating in stage (I) is preferably carried out at a heating rate of from about 0.1 to about 20, preferably from about 0.3 to about 15, in particular from 0.5 to 10, ° C./min.

During this heating phase, the catalyst is heated to a temperature at which the generally organic coatings present there begin to decompose, while at the same time the temperature is controlled by means of the oxygen content and does not increase to an extent which damages the catalyst structure.

After the temperature range of from about 250 to about 800° C., preferably from about 350 to about 600° C., in particular from about 400 to about 600° C., desired for decomposing the coatings has been reached, it is possible—if desired, or if necessary because of the presence of a large amount of organic coatings—to leave the catalyst for a further 1 to 2 hours at these temperatures in the atmosphere defined above.

In stage (I) of the regeneration, with or without the catalyst being left at the steated temperature, the major part of the coatings is carbonized. The substances formed, for example hydrogen, water and carbon-containing substances, are removed from the catalyst in this stage. The removal of the coatings by carbonizing, which is effected in this stage, significantly reduces the quantity of energy liberated during combustion of the catalyst in stages (II) and, if required, (III) of the novel process through treatment of the catalyst with a gas stream which has a relatively high oxygen content, so that an important step toward preventing local overheating of the catalyst is taken simply by the slower heating up in stage (I) of the novel process.

In stage (II) of the novel process, the catalyst is then treated, at from about 250 to about 800° C., preferably from about 350 to about 600° C., with a gas stream which contains from about 0.1 to about 4, preferably from about 0.1 to about 3, particularly preferably from about 0.1 to about 2, % by volume of an oxygen-donating substance or of oxygen or of a mixture of two or more thereof.

The added amount of molecular oxygen or oxygen-donating substances is critical insofar as the quantity of energy liberated within his stage and generated by burning off the carbonized organic coatings results in an increase in the temperature of the catalyst, so that the temperature in the regeneration apparatus must not be outside the desired temperature range of from about 250 to about 800° C., preferably from about 350 to about 600° C. Preferably, the amount of molecular oxygen or oxygen-donating substances is chosen so that the temperature in the apparatus is from about 400 to about 500° C.

As the coatings are increasingly being burnt off, the content of molecular oxygen or oxygen-donating substances in the inert gas stream must be increased up to 100% by volume in order to maintain the temperature required for regeneration, so that, after the end of stage (II), in stage (III) the catalyst is treated, in the temperature range already defined with regard to stage (II), with a gas stream which contains from more than about 4 to 100, preferably from more than about 3 to about 20, particularly preferably from about 2 to about 20, % by volume of an oxygen-donating substance or of oxygen or of a mixture of two or more thereof.

As a rule, a procedure is adopted in which the amount of oxygen or oxygen-donating substance in the gas stream fed in is continuously increased when the temperature in stage (II) decreases.

The temperature of the catalyst as such is kept at from about 250 to about 800° C., preferably from about 350 to about 600° C., in particular from about 400 to about 600° C. by appropriate control of the oxygen content or of the content of oxygen-donating substances in the gas stream.

If the temperature of the exit gas stream at the reactor outlet decreases in spite of increasing amounts of molecular oxygen or oxygen-donating substances in the gas stream, the organic coatings have been completely combusted. The duration of the treatment in stage (II) and, if required, stage (III) is in general from about 1 to about 30, preferably from about 2 to about 20, in particular from about 3 to about 10, hours in each case.

The term oxygen-donating substances used above includes all substances which are capable of donating oxygen or removing carbon-containing residues under the stated regeneration conditions. Particular examples are:

Oxides of nitrogen of the formula $N_xO_y$, where x and y are chosen to give a neutral oxide of nitrogen, $N_2O$, $N_2O$-containing exit gas stream from an adipic acid plant, NO, $NO_2$, ozone or a mixture of two or more thereof. Where carbon dioxide is used as the oxygen-donating substance, stages (II) and (III) are carried out at from 500 to 800° C.

In a further embodiment of the novel process, the partially or completely deactivated catalyst is washed with a solvent, before the heating according to stage (I), in order to remove desired product still adhering. The washing is carried out in such a way that the particular desired products adhering to the catalyst can be removed therefrom but the temperature and pressure are not chosen so high that most organic coating are also removed. Preferably, the catalyst is only rinsed with a suitable solvent.

Thus, suitable solvents for this wash step are all those in which the respective reaction product is readily soluble. Solvents preferably used of this type are selected from the group consisting of water, an alcohol, e.g. methanol, ethanol, 1-propanol, 2-propanol, 2-methyl-2-propanol, 1-butanol, 2-butanol, allyl alcohol or ethylene glycol, an aldehyde, such as acetaldehyde or propionaldehyde, a ketone, e.g. acetone, 2-butanone, 2-methyl-3-butanone, 2-pentanone, 3-pentanone, 2-methyl-4-pentanone or cyclohexanone, an ether, such as diethyl ether or THF, an acid, e.g. formic acid, acetic acid or propionic acid, an ester, such as methyl formate, methyl acetate, ethyl acetate, butyl acetate or ethyl propionate, a nitrile, such as acetonitrile, a hydrocarbon, e.g. propane, 1-butene, 2-butene, benzene, toluene, xylene, trimethylbenzene, dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, dibromoethane, allyl chloride or chlorobenzene, and, if miscible, mixtures of two or more thereof.

Solvents already acting as solvents in the reaction, i.e., for example, the epoxidation of olefin with the use of the catalyst to be regenerated, are preferably used. The following solvents may be mentioned by way of example for the epoxidation of olefins: water, alcohols, e.g. methanol, ethanol, 1-propanol, 2-propanol, 2-methyl-2-propanol, 1-butanol, 2-butanol, allyl alcohol or ethylene glycol, and ketones, such as acetone, 2-butanone, 2-methyl-3-butanone, 2-pentanone, 3-pentanone, 2-methyl-4-pentanone or cyclohexanone.

The amount of solvent used and the duration of the wash step are not critical, but both the amount of solvent and the duration of the wash step should be sufficient to remove a major part of the desired product adhering to the catalyst. The wash step can be carried out at the temperature of the reaction or at comparatively higher temperatures, but the temperature should not be chosen so high that the solvent used for washing itself reacts with the desired product to be removed. If temperatures above the reaction temperature are used, a range of from 5 to 150° C. above the reaction temperature is generally sufficient, in particular because of the boiling point of the solvents used. The wash step can, if required, be repeated several times. The wash step can be carried out under atmospheric, superatmospheric or even supercritical pressure. Atmospheric and superatmospheric pressures are preferred. Where $CO_2$ is used as a solvent, supercritical pressure is preferred.

If a catalyst powder used in a suspension procedure is regenerated, washing of the isolated catalyst is carried out in an external reactor. If the catalyst is packed in the form of a fixed bed in a reactor, the washing can be carried out in the reactor used for the reaction. Said reactor with the catalyst to be regenerated present therein is flushed one or more times with the solvent in order to obtain the residual desired product. The solvent is then removed from the reactor.

After the end of the wash step, the catalyst is generally dried. Although the drying process is not critical per se, the drying temperature should not too greatly exceed the boiling point of the solvent used for washing, in order to avoid abrupt evaporation of the solvent in the pores, in particular—if present—the micropores of the zeolite catalyst, since this too may damage said catalyst. In the regeneration of catalyst powders, drying too is carried out externally in a heating apparatus under an inert gas atmosphere. In the case of catalysts in a fixed bed, the catalyst present in the reactor is treated with an inert gas stream at moderate temperatures. The drying of the catalyst can, but need not, be carried out to completion. In the case of catalyst powders, drying is as a rule continued until the powder is free-flowing. Also in the case of catalysts installed in a fixed bed, complete drying is generally not necessary.

After the regeneration the catalyst may be treated by basic and/or silylating compounds in order to remove acidic centers. Particularly suitable compounds are diluted aqueous solutions of alkaline or alkaline earth hydroxides, alkaline or alkaline earth carbonates, alkaline or alkaline earth hydroxy carbonates; Li, K, Na acetates and phosphates; and silylating esters, such as tetraalkoxy silane, tetraalkoxymonoalkyl silane and hexamethylene disilane.

In a further embodiment of the novel process, the regenerated catalyst obtained in stage (III) is cooled in an inert gas stream in an additional stage (IV). This inert gas stream may contain up to 20, preferably from about 0.5 to about 20, % by volume of a vaporized liquid selected from the group consisting of water, an alcohol, an aldehyde, ketone, an ether, an acid an ester, a nitrile, a hydrocarbon, as described above with regard to the washing of the catalyst, and a mixture of two or more thereof. Water, alcohol or a mixture of two or more thereof is preferably used as the vaporized liquid.

With regard to the alcohols, aldehydes, ketones, ethers, acids, esters, nitriles or hydrocarbons which may preferably be used, reference may be made to the corresponding discussion of the solvents which may be used in the wash step in the novel process.

In the cooling according to stage (IV), too, it is important that cooling is effected slowly since excessively rapid cooling (quenching) may adversely affect the mechanical strength of the catalyst. Furthermore, the mechanical properties of the catalyst may be adversely affected by rapid flushing of the regenerated, dry catalyst molding on restarting the reactor for further reaction. For this reason, it is advisable to add the vaporized liquid defined above during the cooling phase. It is also preferable, however, not to add said vaporized liquid until the temperature is below a threshold temperature which is defined by the boiling point of the liquid used for the vapor. The threshold temperature is as a rule below about 250° C., preferably below about 200° C., in particular below about 150° C.

After the reactor and the regenerated catalyst present therein have been cooled to the reaction temperature, the reactor is filled with the reaction mixture and the reaction is continued. Although in principle all zeolite catalysts can be regenerated within the scope of the present invention, and consequently the zeolite catalysts regenerated by the novel process can also be reused for many reactions, the novel process is preferably used for regenerating zeolite catalysts which are employed in the epoxidation of organic compounds having at least one C—C double bond, for the hydroxylation of aromatic organic compounds or for the conversion of alkanes into alcohols, aldehydes and acids, i.e. for oxidation reactions.

The present invention therefore also relates to the use of a zeolite catalyst regenerated by means of the process described in the present application for the epoxidation of organic compounds having at least one C—C double bond, in particular for the epoxidation of lower olefins of two to six carbon atoms, e.g. ethylene, propylene or 2-butene, for the hydroxylation of aromatic organic compounds or for the conversion of alkanes into alcohols, aldehydes and acids.

EXAMPLES

Example 1

910 g of tetraethyl orthosilicate were introduced into a four-necked flask (4 l capacity) and 15 g of tetraisopropyl orthotitanate were added from a dropping funnel in the course of 30 minutes while stirring (250 rpm, paddle stirrer). A colorless, clear mixture formed. Thereafter, 1600 g of a 20% strength by weight tetrapropylammonium hydroxide solution (alkali metal content<10 ppm) were added and stirring was continued for a further hour. The alcohol mixture (about 900 g) formed from the hydrolysis was distilled off at from 90 to 100° C. The mixture was made up to 3 l with water and the now slightly opaque sol was transferred into a 5 l stainless steel stirred autoclave.

The closed autoclave (anchor stirrer, 200 rpm) was brought to a reaction temperature of 175° C. at a heating rate of 3° C./min. After 92 hours, the reaction was complete. The cooled reaction mixture (white suspension) was centrifuged and the isolated sediment was washed repeatedly with water until it was neutral. The solid obtained was dried at 110° C. in the course of 24 hours (weight obtained: 298 g).

The template which remained in the zeolite was then combusted under air at 550° C. in 5 hours (calcination loss: 14% by weight).

According to wet chemical analysis, the pure white product had a Ti content of 1.5% by weight and a residual alkali content of less than 100 ppm. The yield was 97%, based on $SiO_2$ used. The crystallites had a size of from 0.05 to 0.25 μm and the product had a typical IR band at about 960 $cm^{-1}$.

Example 2

530 g of titanium silicalite powder, synthesized according to Example 1, were kneaded with 13.25 g of silica sol (Ludox AS-40), 26.5 g of Walocel (methylcellulose) and 354 ml of water for 2 h in a kneader. The compacted material was then molded in an extrusion press to give 2 mm strands. The strands obtained were dried at 110° C. for 16 h and then calcined at 500° C. for 5 h.

100 g of the resulting moldings were processed to give chips (particle size 1–2 mm) and used as a catalyst in the epoxidation of propylene with hydrogen peroxide.

Example 3

Streams of 27.5 g/h of hydrogen peroxide (20% by weight), 65 g/h of methanol and 13.7 g/h of propene were passed, at a reaction temperature of 40° C. and a reaction pressure of 20 bar, through a reactor cascade comprising two reactors, each having a reaction volume of 190 ml and each packed with 10 g of catalyst according to Example 2. After leaving the second reactor, the reaction mixture was let down to atmospheric pressure in a Sambay evaporator. The light boilers separated off were analyzed on-line in a gas chromatograph. The discharged liquid reaction mixture was collected, weighed and likewise analyzed by gas chromatography.

During the entire time on-stream, the hydrogen peroxide conversion decreased from originally 98% and reached about 60% after 250 h. The selectivity of propylene oxide with respect to hydrogen peroxide was 95% over the time on-stream

Example 4

The deactivated catalyst from Example 3 was installed in a quartz glass tube. The deactivated catalyst was then heated to 500° C. in a stream of 20 l of nitrogen gas per hour at a heating rate of 4° C./min in a tube furnace. Thereafter, the oxygen content of the inert gas was increased to 9% by volume in the next 2 hours and maintained there. In the next 14 h, the oxygen content was then increased to 18% by volume and maintained there. The regenerated catalyst was then cooled under inert gas, removed and used again for the epoxidation.

Example 5

Streams of 27.5 g/h of hydrogen peroxide (20% by weight), 65 g/h of methanol and 13.7 g/h of propene were passed, at a reaction temperature of 40° C. and a reaction pressure of 20 bar, through a reactor cascade comprising two reactors, each having a reaction volume of 190 ml and each packed with 10 g of regenerated catalyst from Example 4. After leaving the second reactor, the reaction mixture was let down to atmospheric pressure in a Sambay evaporator. The light boilers separated off were analyzed on-line in a gas chromatograph. The discharged liquid reaction mixture was collected, weighed and likewise analyzed by gas chromatography.

During the entire time on-stream, the hydrogen peroxide conversion decreased from originally 98% and reached about 60% after 250 h. The selectivity of propylene oxide with respect to hydrogen peroxide was 95% over the time on-stream.

Example 6

The deactivated catalyst from Example 5 was installed in a quartz glass tube. The deactivated catalyst was then heated to 450° C. in a stream of 20 l of nitrogen gas per hour at a heating rate of 4° C./min in a tube furnace. Thereafter, the oxygen content of the inert gas was increased to 9% by volume in the next 2 hours and maintained there. In the next 14 h, the oxygen content was then increased to 18% by volume and maintained there. The regenerated catalyst was then cooled under inert gas, removed and used again for the epoxidation.

Example 7

Streams of 27.5 g/h of hydrogen peroxide (20% by weight), 65 g/h of methanol and 13.7 g/h of propene were passed, at a reaction temperature of 40° C. and a reaction pressure of 20 bar, through a reactor cascade comprising two reactors, each having a reaction volume of 190 ml and each packed with 10 g of regenerated catalyst from Example 6. After leaving the second reactor, the reaction mixture was let down to atmospheric pressure in a Sambay evaporator. The light boilers separated off were analyzed on-line in a gas chromatograph. The discharged liquid reaction mixture was collected, weighed and likewise analyzed by gas chromatography.

During the entire time on-stream, the hydrogen peroxide conversion decreased from originally 98% and reached about 60% after 250 h. The selectivity of propylene oxide with respect to hydrogen peroxide was 95% over the time on-stream.

The Examples described show that the catalytic activity of the catalysts can be restored without losses by the novel regeneration of the deactivated catalysts.

We claim:

1. A process for regenerating a zeolite catalyst, comprising:
   (I) heating a partially or completely deactivated catalyst to 250–600° C. in an atmosphere which contains less than 2% by volume of oxygen, and
   (II) treating the catalyst at from 250 to 800° C. with a gas stream which contains from 0.1 to 4% by volume of an oxygen-donating substance or of oxygen or of a mixture of two or more thereof, where said gas stream contains a higher amount of oxygen as compared to the atmosphere in (I), wherein
   the heating in (I) is carried out at a heating rate of from 0.1 to 20° C./min.

2. A process as claimed in claim 1, further comprising:
   (III) treating the catalyst at from 250 to 800° C. with a gas stream which contains from more than 4 to 100% by volume of an oxygen-donating substance or of oxygen or of a mixture of two or more thereof.

3. A process as claimed in claim 2, which additionally comprises:
   (IV) cooling of the regenerated catalyst obtained from (III) in an inert gas stream which may contain up to 20% by volume of a vaporized liquid selected from the group consisting of water, an alcohol, an aldehyde, a ketone, an ether, an acid, an ester, a nitrite, a hydrocarbon, and a mixture of two or more thereof.

4. A process as claimed in claim 2, wherein the oxygen-donating substance is $CO_2$ and (II) and (III) are carried out at from 500 to 800° C.

5. A process as claimed in claim 2, wherein the catalyst is treated in (III) at from 350 to 600° C.

6. A process as claimed in claim 1, wherein the partially or completely deactivated catalyst is washed, before the heating in (I), with a solvent selected from the group consisting of water, an alcohol, an aldehyde, a ketone, an ether, an acid, an ester, a nitrile, a hydrocarbon, and a mixture of two or more thereof.

7. A process as claimed in claim 1, wherein the partially or completely deactivated catalyst is kept at from 250 to 800° C. after the heating in (I) and before treatment in (II).

8. A process as claimed in claim 1, wherein the oxygen-donating substance is selected from the group consisting of an oxide of nitrogen of the formula $N_xO_y$, where x and y are chosen to give a neutral oxide of nitrogen, $N_2O$, an $N_2O$ containing exit gas stream from an adipic acid plant, NO, $NO_2$, ozone, and a mixture of two or more thereof.

9. A process as claimed in claim 1, wherein the zeolite catalyst is selected from the group consisting of a titanium-, zirconium-, vanadium-, chromium- or niobium-containing silicalite having the MFI, BEA, MOR, TON, MTW, FER, CHA, ERI, RHO, GIS, BOG, NON, EMT, HEU, KFI, FAI, DDR, MTT, RUT, LTL, MAZ, GME, NES, OFF, SGT, EUO, MFS, MCM-22 or MEL structure, the MFI/MEL mixed structure and a mixture of two or more thereof.

10. A process as claimed in claim 1, wherein the catalyst is treated in (II) at from 350 to 600° C.

11. A process as claimed in claim 1, wherein the heating in (I) is carried out at a heating rate of from 0.3 to 15° C./min.

12. A process as claimed in claim 1, wherein the heating in (I) is carried out at a heating rate of from 0.5 to 10° C./min.

* * * * *